US009187504B2

(12) United States Patent
Stowell et al.

(10) Patent No.: US 9,187,504 B2
(45) Date of Patent: *Nov. 17, 2015

(54) METHOD OF MAKING HYDROXYMETHYLPHOSPHONATE

(75) Inventors: Jeffrey Stowell, Wingdale, NY (US); Ronald L. Pirrelli, Mahopac, NY (US); Ryan Yanosy, Cranberry Township, PA (US)

(73) Assignee: ICL-IP America Inc., Ardsley, NY (US)

( * ) Notice: Subject to any disclaimer, the term of this patent is extended or adjusted under 35 U.S.C. 154(b) by 941 days.

This patent is subject to a terminal disclaimer.

(21) Appl. No.: 13/140,909

(22) PCT Filed: Dec. 16, 2009

(86) PCT No.: PCT/US2009/068196
§ 371 (c)(1),
(2), (4) Date: Jun. 20, 2011

(87) PCT Pub. No.: WO2010/080425
PCT Pub. Date: Jul. 15, 2010

(65) Prior Publication Data
US 2011/0257287 A1    Oct. 20, 2011

(51) Int. Cl.
| C08G 18/16 | (2006.01) |
| C07F 9/40 | (2006.01) |
| C08L 75/04 | (2006.01) |
| C08K 5/5333 | (2006.01) |
| C08J 9/00 | (2006.01) |

(52) U.S. Cl.
CPC ............ *C07F 9/4006* (2013.01); *C08J 9/0038* (2013.01); *C08K 5/5333* (2013.01); *C08L 75/04* (2013.01); *C08J 2375/04* (2013.01)

(58) Field of Classification Search
CPC ..... C07F 9/4006; C08L 75/04; C08K 5/5333; C08J 9/0038; C08J 2375/04
USPC .................... 521/108, 168; 558/114, 118, 119
See application file for complete search history.

(56) References Cited

U.S. PATENT DOCUMENTS

| 2,579,810 | A |   | 12/1951 | Fields |
| 2,593,213 | A |   | 4/1952 | Stiles |
| 3,102,900 | A | * | 9/1963 | Fields ........................... 558/129 |
| 3,179,522 | A | * | 4/1965 | Temin ........................ 106/18.17 |
| 3,382,301 | A |   | 5/1968 | Hechenbleikneret et al. |
| 3,385,801 | A |   | 5/1968 | Birum et al. |
| 3,609,107 | A |   | 9/1971 | Boyer et al. |
| 4,024,207 | A |   | 5/1977 | Biehler et al. |
| 4,697,030 | A |   | 9/1987 | Hardy et al. |
| 4,808,744 | A |   | 2/1989 | Hardy et al. |
| 4,820,854 | A |   | 4/1989 | Hardy et al. |
| 4,883,891 | A |   | 11/1989 | Hardy et al. |
| 4,883,892 | A |   | 11/1989 | Hardy et al. |
| 4,886,895 | A |   | 12/1989 | Hardy et al. |
| 5,097,057 | A |   | 3/1992 | Hardy et al. |
| 5,117,033 | A |   | 5/1992 | Hardy et al. |
| 5,272,128 | A |   | 12/1993 | Rosen et al. |
| 5,952,327 | A |   | 9/1999 | Waldeck et al. |
| 8,198,341 | B2 | * | 6/2012 | Stowell et al. ................ 521/108 |
| 2007/0112084 | A1 |   | 5/2007 | Hansel et al. |
| 2010/0160468 | A1 |   | 6/2010 | Stowell et al. |
| 2014/0309321 | A1 |   | 10/2014 | Stowell et al. |
| 2015/0080487 | A1 |   | 3/2015 | Stowell et al. |

FOREIGN PATENT DOCUMENTS

| CA | 2246634 | 4/1999 |
| EP | 0570706 | 11/1993 |
| EP | 0908464 | 4/1999 |
| GB | 652706 A | 11/1952 |
| GB | 682706 | 11/1952 |
| GB | 1420543 | 1/1976 |
| WO | 2014/056138 A1 | 4/2014 |
| WO | 2014/062313 A2 | 4/2014 |

OTHER PUBLICATIONS

International Search Report and Written Opinion mailed on May 3, 2010.
Ivanov et al, "Reaction in the System Trialkyl Phosphite—Carboxamide or Secondary Amine," Bulletin of the Academy of Sciences of the USSR, Division of Chemical Science, vol. 20, No. 12, Dec. 1971, pp. 2629-2632.
Gajewiak et al, "Synthesis and Molecular Recognition of the Phosphatidylinositol-3-Methylenephosphate," Organic Letters, vol. 8, No. 13, Jun. 22, 2006, pp. 2811-2813.

* cited by examiner

*Primary Examiner* — John Cooney
(74) *Attorney, Agent, or Firm* — Dilworth & Barrese, LLP

(57) ABSTRACT

A method of making hydroxymethylphosphonate comprising heating paraformaldehyde in a solvent to a desired reaction temperature, wherein the solvent is present in at least an amount necessary to solvate or suspend the paraformaldehyde; adding at least one alkyl phosphite to the heated paraformaldehyde, to provide hydroxymethylphosphonate, the alkyl phosphite being added to the heated paraformaldehyde at a rate which will avoid or inhibit the production of a significant exotherm and resulting high/significant level of acid by-product(s), there being present in the reaction medium at least one hindered amine catalyst in which the nitrogen in the amine is directly bound to a secondary and/or tertiary carbon of an organic group; and, optionally, following the completion of the addition, heating the reaction mixture to an elevated temperature.

21 Claims, No Drawings

METHOD OF MAKING HYDROXYMETHYLPHOSPHONATE

This application claims priority to U.S. patent application Ser. No. 12/317,055 filed on Dec. 18, 2008 which is now U.S. Pat. No. 8,198,341.

BACKGROUND OF THE INVENTION

1. Field of the Invention

The present invention relates to a method of making hydroxymethylphosphonates, polyurethane foam-forming compositions containing the same, polyurethane foam formed from the polyurethane foam-forming compositions, and polyurethane foam articles made therefrom.

2. Description of Related Art

Polyurethanes are materials that are suitable for a large number of different applications in the industrial and private sectors. However, their use presents problems whenever it is involved in areas where there is a risk of fire. To modify their fire behavior, flame-retarding agents are usually added to these polyurethane materials. However, the use of certain flame-retarding agents has presented environmental concerns.

Phosphorous compounds are highly effective flame-retarding agents for polyurethane foam, owing to their high phosphorous content and good stability to hydrolysis; such as, for example, phosphonates. Unfortunately, various phosphonates have various processing problems associated with their use. Hydroxyalkylphosphonates have found some use as flame-retarding agents but their use has been severely limited by their low purity, and specifically their content of acidic by-products. Further, the formation of hydroxyalkylphosphonates has previously been conducted very quickly, and in small batches, due to extreme exotherms, which occur in the production of such hydroxyalkylphosphonates, which exotherms can result in the high acid content. Other attempts to produce hydroxyalkylphosphonates have necessitated extremely high reaction temperatures. Still other attempts to produce hydroxyalkylphosphonates have resulted in significant byproducts and/or low product yields. Therefore, there is a need for means for making hydroxyalkylphosphonates, which avoids these quality and processing difficulties.

BRIEF SUMMARY OF THE INVENTION

There is provided herein a method for making hydroxyalkylphosphonate, specifically, hydroxymethylphosphonate(s), which method can effectively be conducted at a rate, which results in a high purity, low acidity product. The hydroxymethylphosphonate made by the method herein has a significantly reduced acidity rendering it significantly advantageous to polyurethane foam applications.

Specifically there is provided herein a method of making hydroxymethylphosphonate comprising heating paraformaldehyde in a solvent to a desired reaction temperature, wherein the solvent is present in at least an amount necessary to solvate or suspend the paraformaldehyde; adding at least one alkyl phosphite to the heated paraformaldehyde, to provide hydroxymethylphosphonate, the alkyl phosphite being added to the heated paraformaldehyde at a rate which will avoid or inhibit the production of a significant exotherm and the resulting significant amount (high level) of acid by-product(s), there being present in the reaction medium at least one hindered amine catalyst, e.g., an amine whose nitrogen atom is directly bound to a secondary and/or tertiary carbon of an organic group, e.g., an alkyl group; and, optionally, following the completion of the addition, heating the reaction mixture to an elevated temperature. It will be understood herein that organic moieties can comprise any linear, branched or cyclic, alkyl groups, alkenyl groups, alkynyl groups, aromatic groups, and any of the aforesaid containing a heteroatom, such as, for example, oxygen, nitrogen, or sulfur, wherein said groups can contain up to about 18 carbon atoms, preferably up to about 12 carbon atoms and most preferably up to about 10 carbon atoms.

DETAILED DESCRIPTION OF THE INVENTION

The inventors herein have unexpectedly discovered that the reaction of alkyl phosphite, with solvated heated paraformaldehyde, can in fact, be conducted at lower reaction temperatures and/or over an extended period of time, by slowly adding the alkyl phosphite to the heated paraformaldehyde, in the presence of a hindered amine catalyst. The use of the generally more costly hindered amine catalyst dramatically reduces the quaternization of such catalyst by the alkyl phosphite component, resulting in a higher purity product. The use of unhindered amines in reactions of dialkyl phosphite and paraformaldehyde has previously required the reaction be run at high speed to avoid the quaternization of the catalyst. To achieve this high speed of reaction to avoid catalyst quaternization, and to accommodate for the high cracking temperature of paraformaldehyde, i.e., about 110 degrees Celsius, typically the reaction components were combined at once and reacted at high temperatures, which high temperature reaction results in undesirable by-products and/or acidic by-products. Such a method of the immediate complete addition of one of the reaction components to the other in the presence of unhindered amine catalyst results in a dramatic reaction exotherm, dramatically limiting the batch size, and causing the resulting product from such a immediate addition to have an unacceptably high level of acidic by-product, e.g., greater than 20 mg KOH/g. The use of hindered amine catalyst in the reaction mixture in which addition of alkyl phosphite to heated solvated paraformaldehyde occurs, allows for a previously unexpected lower reaction temperature, and a previously unexpected possible slower addition, that avoids an excessive exotherm and thus avoids the production of acidic by-products.

It will be understood herein that all ranges herein include all subranges there between and also any combination of endpoints of said ranges.

It will be understood herein that the expression linear or branched divalent alkylene group comprises a saturated linear or branched alkyl group which has sufficient hydrogen atoms removed therefrom to allow the alkyl group to be divalent.

It will be understood herein that the expression linear or branched divalent alkenylene group comprises an alkenyl group which has sufficient hydrogen atoms removed therefrom to allow the alkyl group to be divalent.

Unless indicated otherwise, all weight percentages herein are based on the total weight of the reaction components.

All temperatures herein are room temperature unless indicated otherwise.

The hydroxymethylphosphonate can be any hydroxymethylphosphonate, which is made by the method(s) described herein.

Preferably, the hydroxymethylphosphonate is one or more of the general formula:

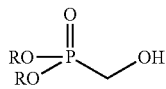

and/or, the general formula:

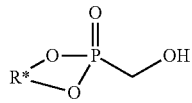

wherein each R is independently the same or different, linear or branched alkyl group of from 1 to about 8 carbon atoms, preferably from 1 to about 6 carbon atoms, and more preferably from 1 to about 3 carbon atoms, linear or branched alkenyl group of from 2 to about 10 carbon atoms, and more preferably from about 3 to about 8 carbon atoms, cycloalkenyl group of from about 5 to about 10 carbon atoms, and more preferably from about 5 to about 8 carbon atoms, and, cycloalkyl group of from about 5 to about 10 carbon atoms, and, more preferably from about 5 to about 8 carbon atoms; and R* is a linear or branched divalent alkylene group of from 2 to about 10 carbon atoms, preferably from 3 to about 8 carbon atoms, linear or branched divalent alkenylene group of from 2 to about 10 carbon atoms, and more preferably from about 3 to about 8 carbon atoms, divalent cycloalkenyl group of from about 5 to about 10 carbon atoms, and more preferably from about 5 to about 8 carbon atoms, and divalent cycloalkyl group of from about 5 to about 10 carbon atoms, and, more preferably from about 5 to about 8 carbon atoms. More preferably, each R is independently selected from the group consisting of methyl, ethyl or propyl. R* preferably is a linear or branched divalent alkylene group containing from 3 to about 8 carbon atoms such as, for example, propylene, 2-methylpropylene, neopentylene or 2-butyl-2-ethylpropylene.

Some examples of hydroxymethylphosphonates can include dimethyl hydroxymethylphosphonate, diethyl hydroxymethylphosphonate, dipropyl hydroxymethylphosphonate, di-isopropyl hydroxymethylphosphonate, methyl ethyl hydroxymethylphosphonate, methyl propyl hydroxymethylphosphonate, methyl isopropyl hydroxymethylphosphonate, ethyl propyl hydroxymethylphosphonate, ethyl isopropyl hydroxymethylphosphonate, propyl isopropyl hydroxymethylphosphonate, dibutyl hydroxymethylphosphonate, dioctyl hydroxymethylphosphonate, propyl pentyl hydroxymethylphosphonate, dicyclohexyl hydroxymethylphosphonate, hydroxymethylphosphonate, 1,3,2-dioxaphosphorinane, 5-methyl-2-(hydroxymethyl), 2-oxide; 1,3,2-dioxaphosphorinane, 5,5-dimethyl-2-(hydroxymethyl), 2-oxide; 1,3,2-dioxaphosphorinane, 5-ethyl-6-propyl-2-(hydroxymethyl), 2-oxide; 1,3,2-dioxaphosphorinane, 5,5-dimethyl-6-isopropyl-2-(hydroxymethyl), 2-oxide; 1,3,2-dioxaphosphorinane, 5-butyl-5-ethyl-2-(hydroxymethyl), 2-oxide and combinations thereof.

The alkyl phosphite herein can be any commercially available alkyl phosphite and specifically is an alkyl phosphite of the general formula:

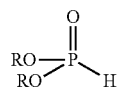

or the general formula:

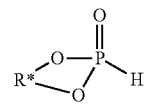

wherein each R is independently the same or different, linear or branched alkyl group of from 1 to about 8 carbon atoms, preferably from 1 to about 6 carbon atoms, and more preferably from 1 to about 3 carbon atoms, linear or branched alkenyl group of from 2 to about 10 carbon atoms, and more preferably from about 3 to about 8 carbon atoms, cycloalkenyl group of from about 5 to about 10 carbon atoms, and more preferably from about 5 to about 8 carbon atoms, and, cycloalkyl group of from about 5 to about 10 carbon atoms, and, more preferably from about 5 to about 8 carbon atoms and R* is a linear or branched divalent alkylene group of from 2 to about 10 carbon atoms, preferably from 3 to about 8 carbon atoms, linear or branched divalent alkenylene group of from 2 to about 10 carbon atoms, and more preferably from about 3 to about 8 carbon atoms, divalent cycloalkenyl group of from about 5 to about 10 carbon atoms, and more preferably from about 5 to about 8 carbon atoms, and divalent cycloalkyl group of from about 5 to about 10 carbon atoms, and, more preferably from about 5 to about 8 carbon atoms. More preferably, each R is independently selected from the group consisting of methyl, ethyl or propyl. R* preferably is a linear or branched divalent alkylene group containing from 3 to about 8 carbon atoms such as, for example, propylene, 2-methylpropylene, neopentylene or 2-butyl-2-ethylpropylene. Alkyl phosphite used in the present invention can be obtained from Rhodia and/or United Phosphorus.

Some examples of alkyl phosphite are selected from the group consisting of dimethyl phosphite, diethyl phosphite, dipropyl phosphite, di-isopropyl phosphite, methyl ethyl phosphite, methyl propyl phosphite, methyl isopropyl phosphite, ethyl propyl phosphite, ethyl isopropyl phosphite, propyl isopropyl phosphite, dibutyl phosphite, dioctyl phosphite, propyl pentyl phosphite, dicyclohexyl phosphite and combinations thereof.

The reaction temperature of the present invention is a temperature that is lower than that which is needed to effect an equivalent reaction between an equivalent alkyl phosphite and paraformaldehyde, but wherein the reaction occurs in the presence of an unhindered amine catalyst. The paraformaldehyde is heated to the reaction temperature prior to the addition of alkyl phosphite. Preferably the reaction temperature is from about 25 degrees Celsius to about 75 degrees Celsius, more preferably from about 30 to about 75 degrees Celsius, even more preferably from about 35 to about 60 degrees Celsius, even more preferably from about 35 to about 55 degrees Celsius, yet even more preferably from about 40 degrees to about 55 degrees Celsius, and most preferably from about 45 degrees to about 55 degrees Celsius. Other preferable reaction temperature ranges can be from 35 degrees Celsius to about 65 degrees Celsius or from 30 degrees Celsius to about 55 degrees Celsius. In one embodiment the reaction temperature can be from about 45 degrees Celsius to about 52 degrees Celsius. Additionally, the reaction temperature herein can be less than room temperature, for example, from about zero degrees Celsius to about 75 degrees Celsius and any from zero degrees Celsius to any of the reaction temperature endpoints provided herein, such as from about zero degrees Celsius to about 55 degrees Celsius and combinations of any of the endpoints listed herein.

The hindered amine catalyst used in the present invention is a tertiary amine in which the nitrogen in the amine is directly bound to a secondary and/or tertiary carbon of an organic group, e.g., an alkyl group, such a hindered amine catalyst will contain at least one such group, preferably two, and even three. It will be understood herein that the use of the expression secondary and/or tertiary carbon of an organic group indicates that at least one organic group which is bound to the nitrogen is a secondary or tertiary organic group, e.g., a secondary or tertiary alkyl group, wherein the central carbon in said secondary or tertiary alkyl group is directly bound to the nitrogen of the amine. It will be understood that such an organic group may in one embodiment contain more than one secondary or tertiary carbon, provided that one of said secondary or tertiary carbons is directly bound to the nitrogen of the amine.

Preferably, the hindered amine catalyst is of the general formula:

wherein each $R^1$, $R^2$ and $R^3$ is each independently the same or different linear, alkyl group containing from one to about 8 carbon atoms, branched alkyl group containing from 3 to about 8 carbon atoms, linear or branched alkenyl group containing up to about 8 carbon atoms, cyclic alkyl group containing from 5 to about 8 carbon atoms, or an aryl group containing from 6 to about 10 carbon atoms, provided that at least one of the $R^1$, $R^2$ and $R^3$ groups is directly bonded to the amine nitrogen by a secondary and/or tertiary carbon atom of said $R^1$, and/or $R^2$, and/or $R^3$ group. Preferably in the hindered amine catalyst of the above general formula at least two of the $R^1$, $R^2$ and $R^3$ groups are attached via a secondary and/or tertiary carbon, and more preferably all three of the $R^1$, $R^2$ and $R^3$ groups are attached via a secondary and/or tertiary carbon. In one non-limiting embodiment herein, each $R^1$, $R^2$ and $R^3$ group of the above general formula of the hindered amine catalyst is independently the same or different and is selected from the group consisting of methyl, ethyl, propyl, butyl, isopropyl, isobutyl, sec-butyl, tert-butyl, isopentyl, neopentyl, isohexyl, isoheptyl, cyclohexyl and phenyl, provided that at least one of the $R^1$, $R^2$ and $R^3$ groups are selected from the group consisting of isopropyl, sec-butyl, tert-butyl, and cyclohexyl. Preferably, at least two of the $R^1$, $R^2$ and $R^3$ groups are selected from the group consisting of isopropyl, sec-butyl, tert-butyl, and cyclohexyl and most preferably, all three of the $R^1$, $R^2$ and $R^3$ groups are selected from the group consisting of isopropyl, sec-butyl, tert-butyl, and cyclohexyl.

Some non-limiting examples of hindered amine catalyst that can be used herein are those selected from the group consisting of triisopropylamine, tri(sec-butyl)amine, tricyclohexylamine, diisopropylmethylamine, diisopropylethylamine, diisopropylpropylamine, di(sec-butyl)methylamine, di(sec-butyl)ethylamine, di(sec-butyl)propylamine, dicyclohexylmethylamine, dicyclohexylethylamine, dicyclohexylpropylamine, diisopropylisobutylamine, diisopropyl(sec-butyl)amine, diisopropylcyclohexylamine, diisopropylphenylamine, diisobutylisopropylamine, diisobutyl(sec-butyl)amine, diisobutylcyclohexylamine, di(sec-butyl)isopropylamine, di(sec-butyl)isobutylamine, di(sec-butyl)cyclohexylamine, di(sec-butyl)phenylamine, dicyclohexylisopropylamine, dicyclohexylisobutylamine, dicyclohexyl(sec-butyl)amine, dicyclohexylphenylamine, diphenylisopropylamine, diphenyl(sec-butyl)amine, diphenylcyclohexylamine, and combinations thereof.

The method of the making hydroxymethylphosphonate herein can comprise heating the paraformaldehyde to the reaction temperature followed by adding the alkyl phosphite thereto, as described herein with respect to the rate of addition, with solvent and hindered amine catalyst present in the reaction medium and/or mixture.

The hindered amine catalyst finds its employment in the reaction mixture in any manner that is most expedient; provided the herein described rate of addition of alkyl phosphite to the paraformaldehyde is maintained (e.g., there is no extreme/significant exotherm), preferably, the hindered amine catalyst is combined with the paraformaldehyde before, during, or after heating the paraformaldehyde, most preferably before said heating. In another less preferable embodiment, the hindered amine catalyst is combined with the alkyl phosphite before or during the addition to paraformaldehyde. In a preferable embodiment, the hindered amine catalyst is present in a reaction vessel prior to the addition of paraformaldehyde thereto. Still further, in another embodiment, the hindered amine catalyst can be combined in part with both the alkyl phosphite and paraformaldehyde prior to reaction thereof. Similarly, the solvent can be added to the reaction medium in like manner as described for the hindered amine catalyst, alone or in combination with the hindered amine catalyst. Preferably, the solvent is added to the paraformaldehyde or the paraformaldehyde is added to the solvent, prior to or during heating of the paraformaldehyde.

Preferably the solvent can be any solvent which effectively solvates or suspends (with stirring) the paraformaldehyde component. Effective solvation or suspension can vary greatly depending on the solvent and the amount of paraformaldehyde employed in the method herein. Preferably, effective solvation/suspension can comprise sufficient solvent to effect solvation/suspension of from 50 weight percent of the paraformaldehyde, based on the total weight of paraformaldehyde, to an amount of solvent that is up to about 100 percent more solvent than is necessary for the complete dissolution/suspension of the total paraformaldehyde being employed, said latter percent being based upon the total amount of solvent necessary to completely solvate/suspend the total amount of paraformaldehyde being employed. Preferably, the amount of solvent present will be sufficient to solvate/suspend from about 75 weight percent of the paraformaldehyde, up to about 25 percent more solvent than is necessary to completely solvate/suspend the total paraformaldehyde being employed. In one embodiment, solvent is used in at least the amount necessary to completely solvate and/or suspend the amount of paraformaldehyde being used.

In one preferable embodiment, the solvent is a hydroxyalkylphosphonate, more preferably a hydroxymethylphosphonate, even more preferably any of the hydroxymethylphosphonates described herein, and most preferably a portion of hydroxymethylphosphonate remaining from a previous batch formed from the reaction method described herein, i.e., a heel of product hydroxymethylphosphonate. In one embodiment, the hydroxyalkylphosphonate can be other than that of a heel of a previous batch. Specifically, the portion of remaining hydroxymethylphosphonate from a previous batch which can effectively operate as a solvent for the paraformaldehyde can comprise from about 0.01 weight percent to about 35 weight percent, preferably from about 5 weight percent to about 30 weight percent, more preferably from about 10 weight percent to about 28 weight percent, and most preferably from about 15 weight percent to about 25 weight percent, said weight percent being based on the total weight of the product hydroxymethylphosphonate of a previous reaction batch that remains in situ, or is provided from the previous reaction vessel.

In another embodiment herein, the solvent can be any other solvent other than hydroxyalkylphosphonate that can effectively solvate/suspend the paraformaldehyde as described above, such as for example, dry solvents. Some non-limiting examples of solvents can comprise toluene, xylene, cyclohexane, n-heptane, hexane, methyl acetate, ethyl acetate, ethanol, propanol, isopropanol, butanol and combinations thereof.

The alkyl phosphite is added to the heated paraformaldehyde at any intermittent and/or continuous rate that will avoid or inhibit a significant/high exotherm which results in a high level of acid by-product(s). Such a rate can be determined by those skilled in the art depending on the specific parameters of the method being practiced, i.e., depending on the specific components, specific amounts and specific reactor limitations available, as well as any processing variables. In one embodiment herein it will be understood that the significant/high exotherm is an exotherm that will produce the high level/significant amount of acid by-products. In one preferable embodiment, an acid by-product is a quaternized amine salt and/or free acid. In one embodiment a significant/high level amount of acid by-product is any amount greater than about 1 percent by weight, more specifically greater than about 5 percent by weight, and most specifically greater than about 10 percent by weight, said percent by weight being based on the total weight of hydroxyalkylphosphonate product.

In one other embodiment of the method herein, the alkyl phosphite is added to the heated paraformaldehyde at any intermittent and/or continuous rate that will produce the reaction product in a purity greater than 90 percent by weight, more preferably greater than about 95 percent by weight, and most preferably greater than about 99 percent by weight, said weight percent being based on the total weight of product hydroxymethylphosphonate. In one embodiment herein the reaction product hydroxyalkylphosphonate is produced in a purity of greater than 90 percent by weight, preferably greater than 95 percent by weight and most preferably greater than about 99 percent by weight, said percent being based on the total weight of reaction product. Such purity is to the exclusion of side-products, specifically, P-III-based side-products, such as trialkyl phosphites. More specifically exclusion of side products is understood to be less than about 10 percent by weight, more preferably less than about 5 percent by weight and most preferably less than about 1 percent by weight of said side-products, said percent by weight being based on the total weight of the hydroxymethylphosphonate reaction product. It is understood that in one embodiment herein that in addition to the avoidance or inhibition of a significant amount of acid by-product (by controlling the exotherm by the control of the rate of addition of the alkyl phosphite to the paraformaldehyde), that the rate and/or order of addition will avoid and/or inhibit the production of the above recited amounts of side-products. Amounts of side-product in excess of 10 percent by weight will negatively effect, the quality of, and/or the ability to make, polyurethane foam made from polyurethane foam-forming compositions containing such side-products.

Preferably, in the method described herein, the method will produce a hydroxymethylphosphonate reaction product wherein the product contains less than about 10 percent by weight of quaternized amine salt and/or free acid, more preferably less than about 5 percent by weight of quaternized amine salt and/or free acid, and most preferably less than about 1 percent by weight of quaternized amine salt and/or free acid based on the total weight of the reaction product.

In one embodiment herein the acid by-products can be avoided or inhibited by the above stated rate, in that the chosen rate can be chosen so as to prevent an extreme/significant exotherm in the method, i.e., an exotherm that cannot effectively be controlled by cooling the reaction medium and/or reaction mixture. Preferably the rate can be chosen so that any resulting exotherm, if any, is not so far in excess of the desired reaction temperature that cooling cannot effectively control it. Effective control comprises maintaining the exotherm at no higher than about 25 degrees Celsius above the desired reaction temperature, preferably no higher than about 20 degrees above the desired reaction temperature, more preferably no higher than about 15 degrees above the desired reaction temperature, even more preferably no higher than about 10 degrees above the reaction temperature and most preferably no higher than about 5 degrees above the reaction temperature. By slow addition of the alkyl phosphite either continuously or intermittently, extreme exotherm can be avoided or dramatically reduced. Preferably, the addition of alkyl phosphite is continuous.

In one embodiment, the alkyl phosphite is added to the heated paraformaldehyde at a rate that maintains the reaction temperature at from about 30 degrees Celsius to about 75 degrees Celsius, more preferably any of the reaction temperature ranges described herein. Preferably, the alkyl phosphite is added to the heated paraformaldehyde at a rate that maintains the reaction temperature at from about 30 degrees Celsius to about 55 degrees Celsius. Alternate range can comprise from about 30 to about 65 degrees Celsius, from about 35 to about 60 degrees Celsius, from about 40 to about 55 degrees Celsius and combinations of any endpoints of said temperature ranges, e.g., from about 30 to about 55 degrees Celsius, and the like.

In one embodiment herein the alkyl phosphite is added to the heated paraformaldehyde over a period of from about 10 minutes to about 24 hours, more preferably from about 15 minutes to about 20 hours, even more preferably from about 20 minutes to about 15 hours, yet even more preferably from about 20 minutes to about 10 hours, yet still even more preferably from about 30 minutes to about 8 hours and most preferably from about 45 minutes to about 5 hours. Such time period ranges include all ranges therebetween and any combination of said endpoints. In one embodiment, the alkyl phosphite is added to the heated paraformaldehyde over a period of from about 10 minutes to about 5 hours.

While the step of using an elevated temperature is not necessary in the method herein, it can be utilized to force the reaction to completion, i.e., the complete or substantial reaction of any (if any) remaining unreacted components following the completion of the addition. It is understood herein that the optional elevated temperature step, if employed, will employ a temperature that is in excess of the desired reaction temperature. Preferably, the elevated temperature can be from any temperature higher than the chosen reaction temperature up to about 85 degrees Celsius. More preferably the elevated temperature is from about 55 to about 75 degrees Celsius, even more preferably from about 60 to about 75 degrees Celsius, and most preferably from about 65 to about 75 degrees Celsius. The elevated reaction temperature can be maintained from about 1 minute to about 5 hours, preferably from about 5 minutes to about 4 hours, more preferably from about 10 minutes to about 3 hours and most preferably from about 30 minutes to about 2.5 hours.

While the amount of paraformaldehyde and alkyl phosphite can vary dramatically depending on the specific reaction components and conditions, solvent, catalyst, desired reaction temperature, and batch size, preferably, the amount of paraformaldehyde and alkyl phosphite can exist in equivalent or near equivalent molar amounts. Near equivalent molar amounts can comprise wherein either the paraformaldehyde or alkyl phosphite is present in a molar excess of the other component. Preferably, either the alkyl phosphite or the paraformaldehyde component can exist in no more than 10 molar percent excess of the other component, more preferably no more than 5 molar percent excess of the other component, and most preferably no more than 3 molar percent excess of the other component. In one preferable embodiment, the paraformaldehyde can be present in about 1 to about 3 molar percent excess of the molar amount of alkyl phosphite. The solvent can be present in the solvating ranges described above but preferably about 5 to about 40 weight percent, more preferably from about 10 to about 30 weight percent and most preferably, from about 15 to about 25 weight percent, said weight percent being based on the total weight of the reaction mixture. The catalyst can be used in amounts of preferably from about 0.5 to about 5.0 weight percent, more preferably from about 1.0 to about 4.0 weight percent, and most preferably from about 2.0 to about 3.0 weight percent. Advantageously, the reaction herein can be conducted in a large batch. Preferably, the large batch comprises wherein the amount of reaction product produced comprises from 100 grams up to about 75,000 pounds, more preferably from about 1 kilogram up to about 65,000 pounds, even more preferably from about 100 kilograms up to about 55,000 pounds and most preferably from about 1000 kilograms up to about 50,000 pounds. The hydroxymethylphosphonate reaction product herein can be advantageously utilized in polyurethane foam-forming compositions as a flame-retardant for the polyurethane foam formed therefrom and/or as a polyol component in the polyurethane-foam forming composition. Such polyurethane foam-forming compositions, and those described herein, made using the hydroxymethylphosphonate made by the method described herein, can be reacted to form polyurethane foams, which foams can be utilized in the construction and formation of various articles such as furniture, bedding, automotive seat cushions, panel, and pour-in-place and spray foam insulation. The hydroxymethylphosphonate reaction product of the method herein can comprise significantly less acidity than an equivalent method that utilizes a non-hindered amine catalyst, e.g., triethylamine, and/or a hydroxyalkylphosphonate solvent, and/or conducts the method at a faster rate than is described herein, and/or at a higher temperature than is described herein; preferably, the hydroxymethylphosphonate reaction product of the method herein can comprise at least 5 percent less acidity, more preferably at least 10 percent less acidity, even more preferably at least 30 percent less acidity and most preferably at least 75 percent less acidity than such an equivalent method; such an equivalent method can in addition or alone comprise the simultaneous and/or immediate or substantially immediate complete addition of the paraformaldehyde and alkyl phosphite components. In one embodiment, the method herein can comprise from about 75 to about 80 percent less acidity than such an equivalent method. Such an immediate addition can comprise time periods less than the time periods described for the method herein. As a result, the polyurethane foam made by reacting the polyurethane foam-forming composition which comprises the hydroxymethylphosphonate made by the method herein contains such lower acidity as is described above. These lower acidity products are advantageous in that the use of a high acidity reaction product in foam neutralizes the amine catalysts normally used in making the foam preventing the normal foam-making process. In many cases, foam cannot be made with these high acidity products. Heretofore hydroxymethylphosphonates made by prior art methods were either not used in polyurethane foam-forming compositions due to the poor quality of foams made by such prior art methods or such hydroxymethylphosphonates required the extensive additional step of purifying the phosphate ester of any acidity and/or side-products prior to their use in polyurethane foam forming compositions and the articles made therefrom, where said purification step(s) dramatically increase the complexity of making polyurethane foams and/or additionally increase the costs of making such foams. The present invention avoids these previously required steps and provides a hydroxymethylphosphonate ester that can be directly used in polyurethane-foam forming compositions and applications without further purification steps, e.g., distillation.

Preferably the hydroxymethylphosphonate made by the method described herein has an acidity of less than about 15 mg KOH/g, more preferably, less than about 10 mg KOH/g, even more preferably, less than about 8 mg KOH/g, and most preferably less than about 6 mg KOH/g.

In one embodiment herein, the product hydroxymethylphosphonate can be used in a polyurethane foam-forming composition without further purification. Preferably, the product hydroxymethylphosphonate can be used in a polyurethane foam-forming composition without further purification when the solvent comprises a heel of hydroxymethylphosphonate from a previous batch as described herein. The heel of hydroxymethylphosphonate avoids and/or reduces any purification that can be necessary or desirable prior to use of the hydroxymethylphosphonate reaction product in polyurethane foam-forming compositions. If a solvent other than hydroxyalkylphosphonate is used herein then, preferably, distillation or any other known purification method can be used prior to use in a polyurethane foam-forming composition to remove the solvent. Advantageously, the hindered amine catalyst of the method herein can be utilized as the catalyst in a polyurethane foam-forming composition, which comprises, polyol (or a hydroxyl-containing component), isocyanate and catalyst. Preferably, the hydroxymethylphosphonate reaction product of the method described herein and the hindered amine catalyst of the method herein can remain in situ and be used in the polyurethane foam-forming composition or can be transferred to another reaction vessel where they are used in a polyurethane reaction-forming composition.

Preferably there is provided herein a polyurethane foam-forming composition comprising a polyol, an isocyanate, a catalyst and the hydroxymethylphosphonate produced by the method described herein. Alternatively, there is also preferably provided a polyurethane foam-forming composition comprising a polyol, an isocyanate, and both the hindered amine catalyst and the product hydroxymethylphosphonate of the method described herein. Further there is provided a polyurethane foam-forming composition comprising an isocyanate, a catalyst and the hydroxymethylphosphonate made by the method herein, wherein the hydroxymethylphosphonate functions as an additional hydroxyl-containing component and/or a flame retardant in the polyurethane foam-forming composition.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above.

EXAMPLES

Example 1

Reaction Procedure Using Diisopropylethylamine as the Hindered Amine Catalyst

The reaction heal (2.5 liters; i.e., product) was added to the 20 liter reactor vessel, followed by the addition 2480 grams of 95% reagent grade paraformaldehyde powder (78.5 moles of paraformaldehyde). After heating the reaction mixture to 50° C., 225 grams of diisopropylethylamine (303 ml, 1.74 moles) were added to the reactor, followed by the slow addition of 10350 grams of diethyl phosphite (9655 ml, 74.9 moles). The diethyl phosphite addition was completed at ~90 grams/minute taking a little less than 2 hours. The reaction temperature was maintained at 50° C. throughout the addition. After completing the addition, the reaction temperature was raised to 75° C. and held for 1-2 hours or until all of the diethyl phosphite was consumed as indicated by $P^{31}$ NMR. After a 1 hour vacuum stripping step on a rotary evaporator to remove any remaining free amine and filtration through a sintered glass filter to remove any solid particulates, the product diethyl hydroxymethylphosphonate was isolated in with an acidity of 6.6 mg KOH/g.

Example 2

Reaction Procedure Using Diisopropylethylamine as the Hindered Amine Catalyst

The reaction heal (50 ml; i.e., product) was added to the 1000 ml reactor vessel, followed by the addition 49.7 grams of 95% reagent grade paraformaldehyde powder (1.58 moles of paraformaldehyde). After heating the reaction mixture to 50° C., 4.5 grams of diisopropylethylamine (6.1 ml, 0.035 moles) were added to the reactor, followed by the slow addition of 207.1 grams of diethyl phosphite (193.2 ml, 1.50 moles). The diethyl phosphite addition was completed in 1.5 hours at a rate of 2.3 grams/minute. The reaction temperature was maintained at 50° C. throughout the addition. After completing the addition, the reaction temperature was raised to 75° C. and held for 1-2 hours or until all of the diethyl phosphite was consumed as indicated by $P^{31}$ NMR. After a 1 hour vacuum stripping step on a rotary evaporator to remove any remaining free amine and filtration through a sintered glass filter to remove any solid particulates, the product diethyl hydroxymethylphosphonate was isolated in with an acidity of 6.7 mg KOH/g.

Example 3

Reaction Procedure Using Diisopropylethylamine as the Hindered Amine Catalyst, with Alkyl Phosphite Addition at 35° C.

The reaction heal (50 ml; i.e., product) was added to the 1000 ml reactor vessel, followed by the addition 49.7 grams of 95% reagent grade paraformaldehyde powder (1.58 moles of paraformaldehyde). After heating the reaction mixture to 35° C., 4.5 grams of diisopropylethylamine (6.1 ml, 0.035 moles) were added to the reactor, followed by the slow addition of 207.1 grams of diethyl phosphite (193.2 ml, 1.50 moles). The diethyl phosphite addition was completed in 1.5 hours at a rate of 2.3 grams/minute. The reaction temperature was maintained at 35° C. throughout the addition. After completing the addition, the reaction temperature was raised to 75° C. and held for 1-2 hours or until all of the diethyl phosphite was consumed as indicated by $P^{31}$ NMR. After a 1-hour vacuum stripping step on a rotary evaporator to remove any remaining free amine and filtration through a sintered glass filter to remove any solid particulates, the product diethyl hydroxymethylphosphonate was isolated in with an acidity of 5.2 mg KOH/g.

Comparative Example 1

Reaction Procedure Using Triethylamine as the Amine Catalyst

Diethyl phosphite (207.1 grams, 193.2 ml, 1.50 moles), 49.7 grams of 95% reagent grade paraformaldehyde powder (1.58 moles of paraformaldehyde) and 5.6 grams of triethylamine (7.7 ml, 0.055 moles) were added to a 1000 ml round bottom flask at room temperature with a reflux column attached. The reaction mixture was heated to 30-40° C. or until the reaction mixture began to exotherm. The temperature of the reaction mixture reached a maximum of 170° C. in 1-2 minutes. Once the exotherm subsided, the reaction mixture was cooled with stirring to room temperature. After a 1-hour vacuum stripping step on a rotary evaporator to remove any remaining free amine and filtration through a sintered glass filter to remove any solid particulates, the product diethyl hydroxymethylphosphonate was isolated with an acidity of 29.0 mg KOH/g.

Comparative Example 2

Reaction procedure using diisopropylethylamine as the hindered amine catalyst (with addition of paraformaldehyde to phosphite) The use of the term "comparative" in the title of this example is directed to the method of adding paraformaldehyde to phosphite, and is not directed to the use of the diisopropylethylamine catalyst.

Diethyl phosphite (207.1 grams, 193.2 ml, 1.50 moles) and 4.5 grams of diisopropylethylamine (6.1 ml, 0.035 moles) were added to a 1000 ml round bottom flask at room temperature with a reflux column attached. After heating the reaction mixture to 50° C., the paraformaldehyde solid (49.7 grams of 95% reagent grade paraformaldehyde powder; 1.58 moles of paraformaldehyde) was added to the reaction mixture over a period of 1 hour (making sure to control the mildly exothermic reaction with cooling) at a rate of ~0.83 grams/minute. Once the addition was complete, the reaction mixture was heated to 75° C. for an additional 2 hours. Upon initial heat-up, an exothermic reaction did take place between the remaining paraformaldehyde and diethyl phosphite and had to be cooled to maintain the desired reaction temperature. After completing the post reaction for 2 hours at 75° C., the reaction mixture was cooled, placed on a rotary evaporator for 1 hour to remove any remaining free amine and filtered through a sintered glass filter to remove any solid particulates. The product was isolated with an acidity of 4.7 mg KOH/g. Analysis by $P^{31}$ NMR showed an impure reaction product containing 10% by weight of P(III)-based sideproducts, wherein said %(percent) by weight is based on the weight of the hydroxymethylphosphonate reaction product.

Comparative Example 3

Exothermic reaction procedure using diisopropylethylamine as the amine catalyst and involving the immediate addition of all alkyl phosphite and paraformaldehyde to the reaction mixture. The use of the term "comparative" in the title of this example is limited to the immediate addition of all alkyl phosphite and paraformaldehyde as compared to the slow addition in the above Examples 1-3 and is not directed to the use of the diisopropylethylamine catalyst.

Diethyl phosphite (207.1 grams, 193.2 ml, 1.50 moles), 49.7 grams of 95% reagent grade paraformaldehyde powder (1.58 moles of paraformaldehyde) and 4.5 grams of diisopropylethylamine (6.1 ml, 0.035 moles) were added to a 1000 ml round bottom flask at room temperature with a reflux column attached. The reaction mixture was heated to 70-80° C. or until the reaction mixture began to exotherm. The temperature of the reaction mixture reached a maximum of 170° C. in 1-2 minutes. Once the exotherm subsided, the reaction mixture was cooled with stirring to room temperature. After a 1-hour vacuum stripping step on a rotary evaporator to remove any remaining free amine and filtration through a sintered glass filter to remove any solid particulates, the product diethyl hydroxymethylphosphonate was isolated with an acidity of 12.1 mg KOH/g.

Comparative Example 4

Reaction Procedure (Similar to Example 2 Above) Using Triethylamine as the Amine Catalyst The reaction heal (50 ml; i.e., product) was added to the 1000 ml reactor vessel, followed by the addition 49.7 grams of 95% reagent grade paraformaldehyde powder (1.58 moles of paraformaldehyde). After heating the reaction mixture to 50° C., 3.5 grams of triethylamine (4.9 ml, 0.035 moles) were added to the reactor, followed by the slow addition of 207.1 grams of diethyl phosphite (193.2 ml, 1.50 moles). The diethyl phosphite addition was completed in 1.5 hours at a rate of 2.3 grams/minute. The reaction temperature was maintained at 50° C. throughout the addition. After completing the addition, the reaction temperature was raised to 75° C. and held for 2 hours. After completing the post reaction for 2 hours at 75° C., the reaction mixture was cooled and filtered through a sintered glass filter under nitrogen to remove the unreacted paraformaldehyde present in the reaction mixture. Analysis of the reaction liquid by $P^{31}$ NMR showed a complex mixture of reaction products with a significant amount of unreacted diethyl phosphite. Based on $P^{31}$ NMR analysis, the reaction mixture consisted of 11.0% the desired product (diethyl hydroxymethylphosphonate), 58.7% unreacted diethyl phosphite and 30.3% unidentified side-products. This example clearly demonstrates the catalyst deactivation issue associated with using a non-hindered amine catalyst (e.g., triethylamine) under controlled reaction conditions.

The invention claimed is:

1. A method of making hydroxymethylphosphonate comprising heating paraformaldehyde in a solvent to a reaction temperature of from zero degrees Celsius to 75 degrees Celsius, wherein the solvent is hydroxyalkylphosphonate and which is present in at least an amount necessary to solvate or suspend the paraformaldehyde; adding at least one alkyl phosphite to the heated paraformaldehyde, to provide hydroxymethylphosphonate, the alkyl phosphite being added to the heated paraformaldehyde at a rate which will maintain an exotherm at no higher than 25 degrees Celsius above the reaction temperature, there being present in the reaction medium at least one hindered amine catalyst; and, optionally, following the completion of the addition, heating the reaction mixture to an elevated temperature.

2. The method of claim 1 wherein the hydroxymethylphosphonate is of the general formula:

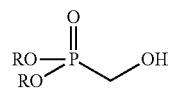

or, the general formula:

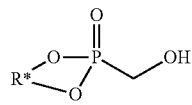

wherein each R is independently the same or different, linear or branched alkyl group of from 1 to about 8 carbon atoms, linear or branched alkenyl group of from 2 to about 10 carbon atoms, cycloalkenyl group of from about 5 to about 10 carbon atoms, and cycloalkyl group of from about 5 to about 10 carbon atoms; and R* is a divalent linear or branched alkylene group of from 2 to about 10 carbon atoms, linear or branched divalent alkenylene group of from 2 to about 10 carbon atoms, divalent cycloalkenyl group of from about 5 to about 10 carbon atoms, and divalent cycloalkyl group of from about 5 to about 10 carbon atoms.

3. The method of claim 1 wherein the alkyl phosphite is of the general formula:

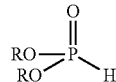

or the general formula:

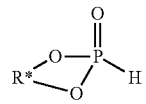

wherein each R is independently the same or different, linear or branched alkyl of from 1 to about 8 carbon atoms, linear or branched alkenyl group of from 2 to about 10 carbon atoms, cycloalkenyl group of from about 5 to about 10 carbon atoms, and, cycloalkyl group of from about 5 to about 10 carbon atoms; and R* is a linear or branched divalent alkylene group of from 2 to about 10 carbon atoms, linear or branched divalent alkenylene group of from 2 to about 10 carbon atoms, divalent cycloalkenyl group of from about 5 to about 10 carbon atoms, and divalent cycloalkyl group of from about 5 to about 10 carbon atoms.

4. The method of claim 1 wherein the reaction temperature is from about 30 degrees Celsius to about 75 degrees Celsius.

5. The method of claim 1 wherein the reaction temperature is from about 35 degrees Celsius to about 60 degrees Celsius.

6. The method of claim 1 wherein the reaction temperature is from about 35 degrees Celsius to about 55 degrees Celsius.

7. The method of claim 1 wherein the hindered amine catalyst is a tertiary amine in which the nitrogen in the amine is directly bound to a secondary and/or tertiary carbon of an organic group.

8. The method of claim 1 wherein the hindered amine catalyst is of the general formula:

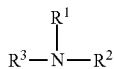

wherein each $R^1$, $R^2$ and $R^3$ is each independently the same or different linear alkyl group containing from one to about 8 carbon atoms, branched alkyl group containing from 3 to about 8 carbon atoms, linear or branched alkenyl group containing up to about 8 carbon atoms, cyclic alkyl group containing from 5 to about 8 carbon atoms, or an aryl group containing from 6 to about 10 carbon atoms, provided that at least one of the $R^1$, $R^2$ and $R^3$ groups are bonded to the nitrogen via a secondary or tertiary carbon of the $R^1$, and/or $R^2$ and/or $R^3$ group.

9. The method of claim 8 wherein each $R^1$, $R^2$ and $R^3$ group is independently the same or different and is selected from the group consisting of methyl, ethyl, propyl, butyl, isopropyl, isobutyl, sec-butyl, tert-butyl, isopentyl, neopentyl, isohexyl, isoheptyl, cyclohexyl and phenyl, provided that at least one of the $R^1$, $R^2$ and $R^3$ groups are selected from the group consisting of isopropyl, sec-butyl, tert-butyl, and cyclohexyl.

10. The method of claim 1 wherein the hindered amine catalyst is selected from the group consisting of triisopropylamine, tri(sec-butyl)amine, tricyclohexylamine, diisopropylmethylamine, diisopropylethylamine, diisopropylpropylamine, di(sec-butyl)methylamine, di(sec-butyl)ethylamine, di(sec-butyl)propylamine, dicyclohexylmethylamine, dicyclohexylethylamine, dicyclohexylpropylamine, diisopropylisobutylamine, diisopropyl(sec-butyl)amine, diisopropylcyclohexylamine, diisopropylphenylamine, diisobutylisopropylamine, diisobutyl(sec-butyl)amine, diisobutylcyclohexylamine, di(sec-butyl)isopropylamine, di(sec-butyl)isobutylamine, di(sec-butyl)cyclohexylamine, di(sec-butyl)phenylamine, dicyclohexylisopropylamine, dicyclohexylisobutylamine, dicyclohexyl(sec-butyl)amine, dicyclohexylphenylamine, diphenylisopropylamine, diphenyl(sec-butyl)amine, diphenylcyclohexylamine, and combinations thereof.

11. The method of claim 1 wherein the alkyl phosphite is added to the heated paraformaldehyde at a rate that maintains the reaction temperature at from about 30 degrees Celsius to about 75 degrees Celsius.

12. The method of claim 1 wherein the alkyl phosphite is added to the heated paraformaldehyde at a rate that maintains the reaction temperature at from about 30 degrees Celsius to about 55 degrees Celsius.

13. The method of claim 1 wherein the alkyl phosphite is added to the heated paraformaldehyde over a period of from about 10 minutes to about 24 hours.

14. The method of claim 1 wherein the alkyl phosphite is added to the paraformaldehyde over a period of from about 10 minutes up to about 5 hours.

15. The method of claim 1 wherein the elevated temperature is sufficient to complete the reaction of any unreacted components.

16. The method of claim 1 wherein the product contains less than about 10 percent by weight of quaternized amine salt and/or free acid.

17. The method of claim 1 wherein the product contains less than about 5 percent by weight of quaternized amine salt and/or free acid.

18. The method of claim 1 wherein the product hydroxymethylphosphonate is produced in a purity of greater than 90 percent by weight.

19. The method of claim 1 wherein the reaction mixture contains less than 10 percent by weight of P-III side-products based on the weight of the hydroxymethylphosphonate.

20. The method of claim 1 wherein the product hydroxymethylphosphonate can be used in a polyurethane foam-forming composition without further purification.

21. The method of claim 1 wherein the reaction is conducted in a large batch.

* * * * *